United States Patent
Mederski et al.

(10) Patent No.: US 7,060,706 B1
(45) Date of Patent: Jun. 13, 2006

(54) QUINAZOLINONES

(75) Inventors: Werner Mederski, Zwingenberg (DE); Ralf Devant, Darmstadt (DE); Gerhard Barnickel, Darmstadt (DE); Sabine Bernotat-Danielowski, Bad Nauheim (DE); Guido Melzer, Hofheim/Taunus (DE); Bertram Cezanne, Mörfelden-Walldorf (DE); Daljit Dhanoa, Del Mar, CA (US); Bao-Ping Zhao, West Windsor, NJ (US); James Rinker, Kenhorst, PA (US); Mark Player, Phoenixville, PA (US); Richard Soll, Lawrencehill, NJ (US)

(73) Assignee: 3-Dimensional Pharmaceuticals, Inc., Exton, PA (US)

( * ) Notice: Subject to any disclaimer, the term of this patent is extended or adjusted under 35 U.S.C. 154(b) by 342 days.

(21) Appl. No.: 10/089,167

(22) PCT Filed: Sep. 13, 2000

(86) PCT No.: PCT/EP00/08939

§ 371 (c)(1),
(2), (4) Date: Aug. 29, 2002

(87) PCT Pub. No.: WO01/23364

PCT Pub. Date: Apr. 5, 2001

Related U.S. Application Data

(60) Provisional application No. 60/325,777, filed on Sep. 28, 1999.

(51) Int. Cl.
C07D 239/91 (2006.01)
A61K 31/517 (2006.01)
A61P 9/10 (2006.01)

(52) U.S. Cl. .................. 514/266.31; 544/287

(58) Field of Classification Search ............. 544/287, 544/284; 514/266.3, 266.31, 266.2
See application file for complete search history.

(56) References Cited

U.S. PATENT DOCUMENTS 5,783,577 A * 7/1998 Houghten et al. .......... 514/247

FOREIGN PATENT DOCUMENTS

WO 98 11438 3/1998

* cited by examiner

*Primary Examiner*—Venkataraman Balasubramanian
(74) *Attorney, Agent, or Firm*—Woodcock Washburn LLP

(57) ABSTRACT

Quinazolinones of formula (I) in which R, $R^1$, $R^2$, $R^3$, $R^4$, Y, n and m have the meaning indicated in Patent claim 1, and their salts or solvates as glycoprotein IbIX antagonists (I)

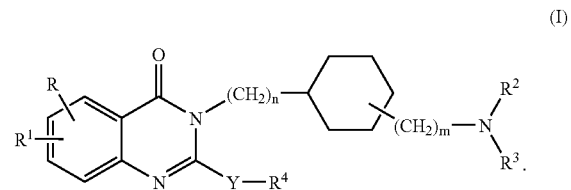

8 Claims, No Drawings

QUINAZOLINONES

This application is a national stage application of PCT/EP00/08939, filed Sep. 13, 2000, which claims priority of provisional application U.S. Ser. No. 60/325,777, filed Sep. 28, 1999.

The invention relates to substituted quinazolinones of the formula I

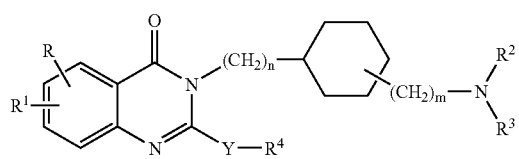

in which
R and $R^1$ are independently of each other H, A, OH, OA, $OCH_2$—Ar, Hal, $NH_2$, NHA, $NA_2$, $NO_2$, CN, $C(O)R^2$, $CONH_2$, CONHA, $CONA_2$, COOH, COOA or $SO_2A$,
$R^2$ and $R^3$ are independently of each other H, A, —C(=NH)—$NH_2$ or solid phase,
$R^4$ is Ar, phenylalkyl, cycloalkyl or Het,
Y may be absent and, if present, is alkenyl having 2 to 4 carbon atoms,
A is unbranched or branched alkyl having 1 to 6 carbon atoms,
Ar is phenyl, naphthyl, biphenyl or benzofuranyl, which is unsubstituted or mono-, di- or trisubstituted by A, OH, OA, $CF_3$, $OCF_3$, Hal, CN, COOH, COOA, $NH_2$, NHA, $NA_2$, $NO_2$, $SO_2NH_2$, $SO_2NAH$ or $SO_2NA_2$,
Het is a saturated, partially or completely unsaturated mono- or bicyclic heterocyclic radical having 5 to 10 ring members, where 1 or 2 N and/or 1 or 2 S or O atoms can be present and the heterocyclic radical can be mono- or disubstituted by A, Hal, OH, OA, $CF_3$, $OCF_3$, $NH_2$, NHA, $NA_2$, COOH, COOA, phenyl which is unsubstituted or mono-, di- or trisubstituted by A, OH, OA, $CF_3$, $OCF_3$, Hal, CN, COOH, COOA, $NH_2$, NHA, $NA_2$, $NO_2$, $SO_2NH_2$, $SO_2NAH$ or $SO_2NA_2$ or thiophenyl which is unsubstituted or mono-, di- or trisubstituted by A, OH, OA, $CF_3$, $OCF_3$, Hal, CN, COOH, COOA, $NH_2$, NHA, $NA_2$, $NO_2$, $SO_2NH_2$, $SO_2NAH$ or $SO_2NA_2$,
Hal is F, Cl, Br or I,
n is 0, 1, 2 or 3,
m is 0, 1, 2 or 3,
and their pharmaceutically tolerable salts and solvates.

Similar compounds having a quinazolinone parent structure as a combinatorial library are disclosed in WO 98/11438. W. D. Dean et al, J. Het. Chem. 1982, 1117–24 and L. Legrand et al, Bull. Soc. Chim. Fr. 1976, 1853–6 describes methods for the synthesis of similar quinazolinone compounds.

The invention is based on the object of finding novel compounds having valuable properties, in particular those which can be used for the production of medicaments.

It has been found that the compounds of the formula I and their salts or solvates have very valuable pharmacological properties together with good tolerability.

They act especially as GPIbIX inhibitors, in particular inhibiting the interaction of this receptor with the ligand von Willebrand factor (vWF). This action can be demonstrated, for example, by a method which is described by S. Meyer et al. in J. Biol. Chem. 1993, 268, 20555–20562. The property as GPIbIX alpha-thrombin receptor (N. J. Greco, Biochemistry 1996, 35, 915–921) can also be blocked by the compounds mentioned.

The significance of GPIbIX as an adhesion receptor on platelets, which mediates the primary interaction of platelets with an arteriosclerotically modified vascular wall via binding to the vWF expressed there, has been described by many authors (e.g. Z. M. Ruggeri in Thromb. Hemost. 1997, 78, 611–616). The activation of another platelet adhesion receptor, GPIIbIIIa, following the GPIbIX-vWF interaction, leads to platelet aggregation and thus to thrombotic vascular occlusion.

A GPIbIX antagonist can thus prevent the start of thrombus formation and thus also release of active substances from the platelets which, for example, promote thrombus growth and have an additional trophic action on the vascular wall. This has been shown with inhibitory peptides or antibodies in various experimental models (e.g. H Yamamoto et al., Thromb. Hemost. 1998, 79, 202–210).

In the case of higher shear forces, the blocking action of GPIbIX inhibitors exerts its maximum effect, as described by J. J. Sixma et al. in Arteriosclerosis, Thrombosis, and Vascular Biology 1996, 16, 64–71. According to the flow chamber method used there, the compounds of the formula I can be characterized as GPIbIX inhibitors in whole blood.

The inhibition of thrombus formation of the GPIbIX inhibitors can be measured by a modified Born method (Nature 1962, 4832, 927–929) using botrocetin or ristocetin as an aggregation stimulant.

The compounds of the formula I according to the invention can therefore be employed as pharmaceutical active compounds in human and veterinary medicine. They act as adhesion receptor antagonists, in particular as glycoprotein IbIX antagonists, and are suitable for the prophylaxis and/or therapy of thrombotic disorders and sequelae deriving therefrom. The preferentially best action is to be expected in the case of thrombotic disorders in the arterial vascular system, but GPIbIX inhibitors also have an effect in the case of thrombotic disorders in the venous vascular bed. The disorders are acute coronary syndromes, angina pectoris, myocardial infarct, peripheral circulatory disorders, stroke, transient ischaemic attacks, arteriosclerosis, reocclusion/restenosis after angioplasty/stent implantation. The compounds can furthermore be employed as anti-adhesive substances where the body comes into contact with foreign surfaces such as implants, catheters or cardiac pacemakers.

Therefore, the invention relates further to compounds of the formula I according to claim 1 and their physiologically acceptable salts or solvates as pharmaceutical active compounds.

The invention relates to compounds of the formula I according to claim 1 and their physiologically acceptable salts or solvates as glycoprotein IbIX antagonists.

Comparison medication introduced onto the market which may be mentioned are aspirin and GPIIbIIIa antagonists.

The invention relates to the compounds of the formula I and their salts or solvates, and to a process for the preparation of these compounds and their salts or solvates, characterized in that a) a compound of the formula I is liberated from one of its functional derivatives by treating with a solvolysing or hydrogenolysing agent, or b) in stage 1) a compound of the formula II

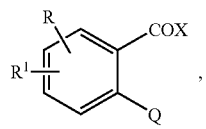
II in which
X is Cl, Br, OH or a reactive esterified OH group and
Q is NH₂ or NHA, either of which is optionally protected, and
R and R¹ are optionally protected when they are or contain NH₂ or NHA, is reacted with a compound of the formula III

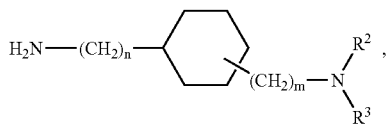
III in which $R^2$, $R^3$, n and m have the meanings indicated in claim 1, to give a compound of formula IV

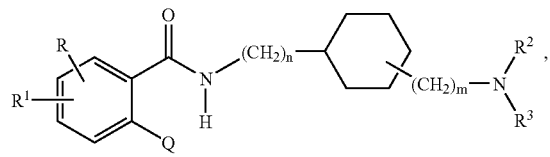
IV in which R, $R^1$, $R^2$, $R^3$, Q, n and m have the meanings indicated above, and
in stage 2) a compound of formula IV as indicated above is if necessary deprotected to give a compound of formula IV in which Q is NH₂ or NHA and is reacted with a compound of formula V

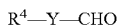 V in which $R^4$ and Y have the meanings indicated in claim 1, or
c) a radical R, $R^1$, $R^2$, $R^3$ and/or $R^4$ is converted into another radical R, $R^1$, $R^2$, $R^3$ and/or $R^4$ by, for example
  converting an amino group into a guanidino group by reaction with an amidinating agent,
  reducing a nitro group, sulfonyl group or sulfoxyl group,
  etherifying an OH group or subjecting an OA group to ether cleavage,
  alkylating a primary or secondary amino group,
  partially or completely hydrolysing a CN group,
  cleaving an ester group or esterifying a carboxylic acid radical,
  reacting an aryl bromide, aryl iodide, heteroaryl bromide or heteroaryliodide to give the corresponding coupling products by means of a Suzuki coupling with boronic acids,
  or carrying out a nucleophilic or electrophilic substitution, and/or a base or acid of the formula I is converted into one of its salts or solvates.

The compounds of the formula I can have a chiral centre and therefore occur in a number of stereoisomeric forms. All these forms (e.g. R and S forms) and their mixtures (e.g. the RS forms) are included in the formula I.

The compounds according to the invention also include so-called prodrug derivatives, i.e. compounds of the formula I modified with, for example, alkyl or acyl groups, sugars or oligopeptides and which are rapidly cleaved in the body to give the active compounds according to the invention.

Furthermore, free amino groups as substituents of compounds of the formula I can be provided with appropriate conventional protective groups. Solvates of the compounds of the formula I are understood as meaning adducts of inert solvent molecules to the compounds of the formula I which are formed on account of their mutual power of attraction. Solvates are, for example, mono- or dihydrates or alcoholates.

The abbreviations used have the following meanings:
BOC tert-butoxycarbonyl,
CBZ benzyloxycarbonyl,
DBU 1,8-diazabicyclo[5.4.0]undec-7-ene,
DCC dicyclohexylcarbodiimide,
DCE dichloroethane,
DDQ 2,3-dichloro-5,6-dicyano-1,4-benzoquinone,
DMA dimethylacetamide,
DMF dimethylformamide,
dppf 1,1'-bis(diphenylphosphino)ferrocene,
Et ethyl,
Fmoc fluorenylmethoxycarbonyl,
HBTU O-(benzotriazolyl)-N,N,N',N'-tetramethyluronium hexafluoro phosphate,
Me methyl,
Mtr 4-methoxy-2,3,6-trimethylphenylsulfonyl,
OBut tert-butyl ester,
OMe methyl ester,
OEt ethyl ester,
POA phenoxyacetyl,
Ph phenyl,
TEA triethylamine,
TFA trifluoroacetic acid.

In the above formulae, A is alkyl and has 1 to 6, preferably 1, 2, 3 or 4 C atoms. Alkyl is preferably methyl, furthermore ethyl, propyl, isopropyl, butyl, isobutyl, sec-butyl or tert-butyl, additionally also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1-or 2-ethylbutyl, 1-ethyl-1-methylpropyl, 1-ethyl-2-methylpropyl, 1,1,2- or 1,2,2-trimethylpropyl.

A is preferentially methyl.

Alkenyl having 2 to 4 carbon atoms is preferably vinyl or buta-1,3-dienyl; vinyl is particularly preferred.

Ar is phenyl, naphthyl, biphenyl or benzofuranyl, which is unsubstituted or mono-, di- or trisubstituted by A, OH, OA, CF₃, OCF₃, Hal, CN, COOH, COOA, NH₂, NHA, NA₂, NO₂, SO₂NH₂, SO₂NAH or SO₂NA₂.

Ar is preferentially phenyl, preferably—as indicated—mono- di- or trisubstituted phenyl, specifically preferentially phenyl, 2-, 3- or 4-methylphenyl, 2-, 3- or 4-ethylphenyl, 2-, 3- or 4-propylphenyl, 2-, 3- or 4-isopropylphenyl, 2-, 3- or 4-tert-butylphenyl, 2-, 3- or 4-aminophenyl, 2-, 3- or 4-N,N-dimethylaminophenyl, 2-, 3- or 4-sulfonamidophenyl, 2-, 3- or 4-nitrophenyl, 2-, 3- or 4-hydroxyphenyl, 2-, 3- or 4-methoxyphenyl, 2-, 3- or 4-ethoxyphenyl, 2-, 3- or 4-trifluoromethylphenyl, 2-, 3- or 4-trifluoromethoxyphenyl, 2-, 3- or 4-carboxyphenyl, 2-, 3- or 4-cyanophenyl, 2-, 3- or 4-fluorophenyl, 2-, 3- or 4-chlorophenyl, 2-, 3- or 4-bromophenyl. Furthermore Ar is preferentially unsubstituted naphthyl, biphenyl or benzofuran-5-yl.

Phenyl, 2-methylphenyl, 3-methylphenyl, 4-methylphenyl, 4-tert-butylphenyl, 4-dimethylaminophenyl, 4-methoxyphenyl, 3-methoxyphenyl, 3-chlorophenyl, 3,4,5-trimethoxyphenyl, 3,4-dimethoxyphenyl, 2,5-dimethoxyphenyl, 3',5'-dimethoxybiphenyl-4-yl, 2',4'-dimethoxybiphenyl-4-yl, biphenyl-4-yl, naphthalen-1-yl, naphthalen-2-yl or benzofuran-5-yl is particularly preferred for Ar.

Cycloalkyl preferably has 3–7 C atoms and is preferably cyclopropyl or cyclobutyl, furthermore preferably cyclopentyl or cyclohexyl, and further also cycloheptyl; cyclohexyl is particularly preferred.

Hal is preferably F, Cl or Br.

Het is a saturated, partially or completely unsaturated mono- or bicyclic heterocyclic radical having 5 to 10 ring members, where 1 or 2 N and/or 1 or 2 S or O atoms can be present and the heterocyclic radical can be mono- or disubstituted by A, Hal, OH, OA, $CF_3$, $OCF_3$, $NH_2$, NHA, $NA_2$, COOH, COOA, phenyl which is unsubstituted or mono-, di- or trisubstituted by A, OH, OA, $CF_3$, $OCF_3$, Hal, CN, COOH, COOA, $NH_2$, NHA, $NA_2$, $NO_2$, $SO_2NH_2$, $SO_2NAH$ or $SO_2NA_2$ or thiophenyl which is unsubstituted or mono-, di- or trisubstituted by A, OH, OA, $CF_3$, $OCF_3$, Hal, CN, COOH, COOA, $NH_2$, NHA, $NA_2$, $NO_2$, $SO_2NH_2$, $SO_2NAH$ or $SO_2NA_2$.

Het is preferably substituted by A, OH, CA, $CF_3$, $OCF_3$, Hal, CN, COOH, COOA, $NH_2$, NHA, $NA_2$, $NO_2$, $SO_2NH_2$, $SO_2NAH$ or $SO_2NA_2$ or thiophenyl which is unsubstituted or mono-, di- or trisubstituted by A, OH, OA, $CF_3$, $OCF_3$, Hal, CN, COOH, COOA, $NH_2$, NHA, $NA_2$, $NO_2$, $SO_2NH_2$, $SO_2NAH$ or $SO_2NA_2$ or unsubstituted 2- or 3-furyl, 2- or 3-thiophenyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, 4- or -5-yl, 1,2,4-triazol-1-, -4- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-1H-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, -4-, 5-, 6- or 7-benzisothiazolyl, 4-, 5-, 6- or 7-benz-2, 1,3-oxadiazolyl, 1-, 2-, 3-, 4-, 5-, 6-, 7- or 8-quinolinyl, 1-, 3-, 4-, 5-, 6-, 7- or 8-isoquinolinyl, 1-, 2-, 3-, 4- or 9-carbazolyl, 1-, 2-, 3-, 4-, 5-, 6-, 7-, 8- or 9-acridinyl, 3-, 4-, 5-, 6-, 7- or 8-cinnolinyl, 2-, 4-, 5-, 6-, 7- or 8-quinazolinyl. The heterocyclic radicals can also be partially or completely hydrogenated. Het can thus also be 2,3-dihydro-2-, -3-, 4- or -5-furyl, 2,5-dihydro-2-, -3-, 4- or -5-furyl, tetrahydro-2- or -3-furyl, 1,3-dioxolan-4-yl, tetrahydro-2- or -3-thienyl, 2,3-dihydro-1-, -2-, -3-, 4 or -5-pyrrolyl, 2,5-dihydro-1-, -2-, -3-, 4- or -5-pyrrolyl, 1-, 2- or 3-pyrrolidinyl, tetrahydro-1-, -2- or -3-pyrrolyl, tetrahydro-1-, -2- or 4-imidazolyl, 2,3-dihydro-1-, -2-, -3-, 4-, -5-, 6-, -7-1H-indolyl, 2,3-dihydro-1-, -2-, -3-, 4- or -5-pyrazolyl, tetrahydro-1-, -3- or 4-pyrazolyl, 1,4-dihydro-1-, -2-, -3- or 4-pyridyl, 1,2,3,4-tetrahydro-1-, -2-, -3-, -4-, -5- or -6-pyridyl, 1,2,3,6-tetrahydro-1-, -2-, -3-, 4-, -5- or -6-pyridyl, 1-, 2-, 3- or 4-piperidinyl, 1-, 2-, 3- or 4-azepanyl, 2-, 3- or 4-morpholinyl, tetrahydro-2-, -3- or 4-pyranyl, 1,4-dioxanyl, 1,3-dioxan-2-, 4- or -5-yl, hexahydro-1-, -3- or -4-pyridazinyl, hexahydro-1-, -2-, 4- or -5-pyrimidinyl, 1-, 2- or 3-piperazinyl, 1,2,3,4-tetrahydro-1-, -2-, -3-, 4-, -5-, -6-, -7- or -8-quinolinyl, 1,2,3,4-tetrahydro-1-, -2-, -3-, -4-, -5-, -6-, -7- or -8-isoquinolinyl.

2-Furyl, thiophen-2-yl, thiophen-3-yl, 5-(3,4-dimethoxyphenyl)-thiophen-2-yl or 5-[2,2]bithiophenyl is particularly preferred for Het.

Phenylalkyl preferably has 7, 8, 9 or 10 carbon atoms and is preferably phenylmethyl, phenylethyl, phenylpropyl or phenylbutyl; phenylethyl is particularly preferred.

The term solid phase indicates a resin for solid-phase chemistry, especially for combinatorial chemistry, i.e. by robot- and computer-assisted syntheses, and subjected to mass screening as indicated in U.S. Pat. No. 5,463,564; M. A. Gallop et al., J. Med. Chem. 1994, 37, 1233–1251 and 1385–1401 and M. J. Sofia, Drugs Discovery Today 1996, 1, 27–34). The polymeric material of the solid phase is generally chosen from the group consisting of cross-linked polystyrene, cross-linked polyacrylamide or other resins, natural polymers or silicagels.

The group of cross-linked polystyrene, cross-linked polyacrylamide or other resins includes e.g. polyacrylamide, polymethacrylamide, polyhydroxyethylmethacrylate, polyamide, polystyrene, (meth)acrylate copolymers, for instance from (methy)acrylic acid, esters of (meth)acrylic acid and/or 2-methylene-succinic acid, but-2-enoic acid or maleic acid, polyurethanes or other copolymers.

Suitable terminal functional groups or linkers on the surface of the resin have to be chosen to attach the compounds to the resin. There exists a variety of commercially available resins, e.g. in Novabiochem—The Combinatorial Chemistry Catalog, March 99. Examples for suitable resins are carbonate resins with a modified carbonate group as terminal functional group like p-nitrophenylcarbonate resin, halogenated resins like Merrifield resin (chloromethylpolystyrene) or carboxy resins like carboxy polystyrene resin or NovaSyn® TG Carboxy Resin. p-Nitrophenylcarbonate resin is particularly preferred. These and other types of resins well known in the art can be used in the subject invention.

R and $R^1$ are independently of each other H, A, OH, OA, $OCH_2$—Ar, Hal, $NH_2$, NHA, $NA_2$, $NO_2$, CN, $C(O)R^2$, $CONH_2$, CONHA, $CONA_2$, COOH, COOA or $SO_2A$, where A, Ar, Hal have a preferred meaning indicated beforehand and $R^2$ has a preferred meaning indicated in the following.

R is preferentially H.

$R^1$ is preferentially H, A, OA or Hal.

The preferred position of $R^1$ is the 6- or 7-position of the quinazolinone ring system.

$R^2$ and $R^3$ are independently of each other H, A, —C(═NH)—$NH_2$ or a solid phase, where A or solid phase have a preferred meaning indicated beforehand.

$R^2$ is preferentially H.

$R^3$ is preferentially H or —C(═NH)—$NH_2$, particularly preferred is H.

$R^4$ is Ar, phenylalkyl, cycloalkyl or Het, where Ar, phenylalkyl, cycloalkyl or Het have a preferred meaning indicated beforehand. $R^4$ is preferentially phenyl, 2-methylphenyl, 3-methylphenyl, 4-methylphenyl, 4-tert-butylphenyl, 4-dimethylaminophenyl, 4-methoxyphenyl, 3-methoxyphenyl, 3-chlorophenyl, 3,4,5-trimethoxyphenyl, 3,4-dimethoxyphenyl, 2,5-dimethoxyphenyl, 3',5'-dimethoxybiphenyl-4-yl, 2',4'-dimethoxybiphenyl-4-yl, biphenyl-4-yl, naphthalen-1-yl, naphthalen-2-yl or benzofuran-5-yl, phenylethyl, cyclohexyl, 2-furyl, thiophen-2-yl, thiophen-3-yl, 5-(3,4-dimethoxyphenyl)-thiophen-2-yl or 5-[2,2']-bithiophenyl.

Y may be absent and, if present, is alkenyl having 2 to 4 carbon atoms Y is preferentially absent or vinyl.

n and m are each independently of each other 0, 1, 2 or 3, particularly preferred 1.

Some preferred groups of compounds can be expressed by the following subformulae Ia to Im, which correspond to the formula I and in which the radicals not designated in greater detail have the meanings indicated in formula I, but in which in Ia
  R is H and
  $R^1$ is H, A, OA or Hal;
in Ib
  R is H,
  $R^1$ is H, A, OA or Hal and
  Y is absent;
in Ic
  R is H,
  $R^1$ is H, A, OA or Hal and
  Y is alkenyl having 2 to 4 carbon atoms;
in Id
  R is H,
  $R^1$ is H, A, OA or Hal,
  $R^2$ is H and
  $R^4$ is Ar;
in Ie
  R is H,
  $R^1$ is H, A, OA or Hal,
  $R^2$ is H and
  $R^4$ is phenylalkyl;
in If
  R is H,
  $R^1$ is H, A, OA or Hal,
  $R^2$ is H and
  $R^4$ is cycloalkyl;
in Ig
  R is H,
  $R^1$ is H, A, OA or Hal,
  $R^2$ is H and
  $R^4$ is Het;
in Ih
  R is H,
  $R^1$ is H, A, OA or Hal,
  $R^2$ is H,
  $R^3$ is H,
  $R^4$ is phenyl, 2-methylphenyl, 3-methylphenyl, 4-methylphenyl, 4-tert-butylphenyl, 4-dimethylaminophenyl, 4-methoxyphenyl, 3-methoxyphenyl, 3-chlorophenyl, 3,4,5-trimethoxyphenyl, 3,4-dimethoxyphenyl, 2,5-dimethoxyphenyl, 3',5'-dimethoxy-biphenyl-4-yl, 2',4'-dimethoxybiphenyl-4-yl, biphenyl-4-yl, naphthalen-1-yl, naphthalen-2-yl or benzofuran-5-yl, phenylethyl, cyclohexyl, 2-furyl, thiophen-2-yl, thiophen-3-yl, 5-(3,4-dimethoxyphenyl)-thiophen-2-yl or 5-[2,2'] bithiophenyl,
  n is 1 and
  m is 1;
in Ik
  R is H,
  $R^1$ is H, A, OA or Hal,
  $R^2$ is H,
  $R^3$ is H,
  Y is —CH=CH—,
  $R^4$ is phenyl, 4-dimethylaminophenyl or 2,5-dimethoxyphenyl,
  n is 1 and
  m is 1;
in Im
  R is H,
  $R^1$ is H, A, OA or Hal,
  $R^2$ is H,
  $R^3$ is H,
  Y is absent,
  $R^4$ is phenyl, 2-methylphenyl, 3-methylphenyl, 4-methylphenyl, 4-tert-butylphenyl, 4-methoxyphenyl, 3-methoxyphenyl, 3-chlorophenyl, 3,4,5-trimethoxyphenyl, 3,4-dimethoxyphenyl, 3',5'-dimethoxybiphenyl-4-yl, 2',4'-dimethoxybiphenyl-4-yl, biphenyl-4-yl, naphthalen-1-yl, naphthalen-2-yl or benzofuran-5-yl, phenylethyl, cyclohexyl, 2-furyl, thiophen-2-yl, thiophen-3-yl, 5-(3,4-dimethoxyphenyl)-thiophen-2-yl or 5-[2,2'] bithiophenyl,
  n is 1 and
  m is 1.

The compounds of the formula I and also the starting substances for their preparation are otherwise prepared by methods known per se, such as are described in the literature (e.g. in the standard works such as Houben-Weyl, Methoden der organischen Chemie [Methods of Organic Chemistry], Georg-Thieme-Verlag, Stuttgart), namely under reaction conditions which are known and suitable for the reactions mentioned. In this case, use can also be made of variants which are known per se, but not mentioned here in greater detail.

The starting substances, if desired, can also be formed in situ such that they are not isolated from the reaction mixture, but immediately reacted further to give the compounds of the formula I.

The compounds of the formula I can be obtained by liberating them from their functional derivatives by solvolysis, in particular hydrolysis or by hydrogenolysis.

Preferred starting substances for the solvolysis or hydrogenolysis are those which otherwise correspond to the formula I, but instead of one or more free amino and/or hydroxyl groups contain corresponding protected amino and/or hydroxyl groups, in particular those which instead of an H—N— group carry an R'—N— group, in which R' is an amino protective group and/or those which instead of the H atom of a hydroxyl group carry a hydroxyl protective group, e.g. those which correspond to the formula I, but instead of a group —COOH carry a group —COOR", in which R" is a hydroxyl protective group.

A number of—identical or different—protected amino and/or hydroxyl groups can also be present in the molecule of the starting substance. If the protective groups present are different from one another, in many cases they can be removed selectively (lit.: T. W. Greene, P. G. M. Wuts, *Protective Groups in Organic Chemistry*, 2nd ed., Wiley, New York 1991, P. J. Kocienski, *Protecting Groups*, 1st ed., or Georg Thieme Verlag, Stuttgart—New York, 1994).

The expression "amino protective group" is generally known and relates to groups which are suitable for protecting (for blocking) an amino group against chemical reactions, but which are easily removable after the desired chemical reaction has been carried out at other positions in the molecule. Typical groups of this type are, in particular, unsubstituted or substituted acyl, aryl, aralkoxymethyl or aralkyl groups. Since the amino protective groups are removed after the desired reaction (or reaction sequence), their nature and size is otherwise not critical; however, those having 1–20, in particular 1–8, C atoms are preferred. The expression "acyl group" is to be interpreted in the widest sense in connection with the present process. It includes acyl groups derived from aliphatic, araliphatic, aromatic or heterocyclic carboxylic acids or sulfonic acids and, in particular alkoxycarbonyl groups, aryloxycarbonyl groups and especially aralkoxycarbonyl groups. Examples of acyl groups of this type are alkanoyl such as acetyl, propionyl, butyryl; aralkanoyl such as phenylacetyl; aroyl such as benzoyl or toluyl; aryloxyalkanoyl such as POA; alkoxycarbonyl such as methoxycarbonyl, ethoxycarbonyl, 2,2,2-trichloroethoxycarbonyl, BOC, 2-iodoethoxycarbonyl; aralkyloxycarbonyl such as CBZ ("carbobenzoxy"), 4-methoxybenzyloxycarbonyl (MOZ), 4-Nitrobenzyloxycarbonyl oder 9-fluorenylmethoxycarbonyl (Fmoc); 2-(phenylsulfonyl)ethoxycarbonyl; trimethylsilylethoxycarbonyl (Teoc) or arylsulfonyl such as 4-methoxy-2,3,6-trimethylphenyl-sulfonyl (Mtr). Preferred amino protective groups are BOC, furthermore CBZ, Fmoc, benzyl and acetyl; particularly preferred Fmoc.

The expression "hydroxyl protective group" is also generally known and relates to groups which are suitable for protecting a hydroxyl group against chemical reactions, but which are easily removable after the desired chemical reaction has been carried out at other positions in the molecule.

Typical groups of this type are the abovementioned unsubstituted or substituted aryl, aralkyl, aroyl or acyl groups, furthermore also alkylgroups, alkyl-, aryl- or aralkylsilylgroups or O,O— or O,S-acetals. The nature and size of the hydroxyl protective groups is not critical, since they are removed again after the desired chemical reaction or reaction sequence; groups having 1–20, in particular 1–10 C atoms, are preferred. Examples of hydroxyl protective groups are, inter alia, benzyl, 4-methoxybenzyl oder 2,4-dimethoxybenzyl, aroyl groups such as benzoyl or p-nitrobenzoyl, acyl groups such as acetyl or pivaloyl, p-toluolsulfonyl, alkyl groups such as methyl or tert-butyl, but also allyl, alkylsilyl groups such as trimethylsilyl (TMS), triisopropylsilyl (TIPS), tert-butyidimethylsilyl (TBS) or triethylsilyl, trimethylsilylethyl, aralkylsilyl groups such as tert-butyldiphenylsilyl (TBDPS), cyclic acetals such as isopropylidene-, cyclopentylidene-, cyclohexylidene-, benzylidene-, p-methoxybenzylidene- or o,p-dimethoxybenzylideneacetal, acyclic acetales such as tetrahydropyranyl (Thp), methoxymethyl (MOM), methoxyethoxymethyl (MEM), benzyloxymethyl (BOM) or methylthiomethyl (MTM). Acetyl, benzyl, tert-butyl or TBS being particularly preferred.

The liberation of the compounds of the formula I from their functional derivatives depending on the protective group used is known in the present literature such as T. W. Greene, P. G. M. Wuts, *Protective Groups in Organic Chemistry*, 2nd ed., Wiley, New York 1991, P. J. Kocienski, *Protecting Groups*, 1st ed., Georg Thieme Verlag, Stuttgart-New-York, 1994. In this case, use can also be made of variants which are known per se, but not mentioned here in greater detail.

The groups BOC and O-tert-butyl can preferably be removed, for example, using TFA in dichloromethane or using approximately 3 to 5N HCl in dioxane at 15–30° C., the Fmoc group using an approximately 5 to 50% solution of dimethylamine, diethylamine or piperidine in DMF at 15–30° C.

Preferred starting substances for the solvolysis or hydrogenolysis includes also those which otherwise correspond to the formula I but are attached to a solid phase. The liberation of the compounds of the formula I from the solid phase is known in the present literature such as Novabiochem—The Combinatorial Chemistry Catalog, March 99 and cited literature.

The solid phase with a carbonate moiety as terminal functional group can preferably be removed, for example, using TFA (50%) in dichloromethane.

The quinazolinones of formula I can also preferably be prepared, using either solution or solid-phase techniques, by combining and reacting an anthranilic acid of formula II with an amine of formula III and if necessary deprotect the given formula IV in which Q is then $NH_2$ or NHA and reacting the compound of formula IV in which Q is $NH_2$ or NHA with an aldehyde of formula V.

As a rule, the starting compounds of the formulae II, III and V are known or commercially available.

The unknown compounds, however, can be prepared by methods known per se. The compounds of the formula II are anthranilic acids. It is furthermore possible to introduce appropriate substituents into the aromatic by conventional electrophilic or alternatively nucleophilic substitutions. Examples of Fmoc protected anthranilic acids, include, but are not limited to, Fmoc protected anthranilic acid, Fmoc protected 3-methyl anthranilic acid, Fmoc protected 3-methoxy anthranilic acid, Fmoc protected 3-chloro anthranilic acid or Fmoc protected 4-chloro anthranilic acid.

Solid-phase techniques may be employed to condense anthranilic acids of formula II and the amine component of formula III which is resin bound ($R^2$ or $R^3$ is solid phase).

The amines of formula III in which $R^2$ or $R^3$ are H, as a rule, are also commercially available and can be attached to the suitable resin by coupling procedures well known in the art and as described in the ensuing Examples. Furthermore, syntheses for the preparation of amines of formula III, such as, for example, the Gabriel synthesis, can be used.

The aldehydes of formula V, as a rule, are also commercially available. Furthermore, syntheses for the preparation of aldehydes of formula V, such as, for example, the oxidation of an alcohol, can be used.

As a rule, the reactions and the attachment to the resin are carried out in an inert solvent. Depending on the conditions used, the reaction time is between a few minutes and a number of days, the reaction temperature between approximately 0° and 150° C., normally between 20° and 130° C.

Suitable inert solvents are, for example, hydrocarbons such as hexane, petroleum ether, benzene, toluene or xylene; chlorinated hydrocarbons such as trichloroethylene, 1,2-dichloroethane, carbon tetrachloride, chloroform or dichloromethane; alcohols such as methanol, ethanol, isopropanol, n-propanol, n-butanol or tert-butanol; ethers such as diethyl ether, diisopropyl ether, tetrahydrofuran (THF) or dioxane; glycol ethers such as ethylene glycol monomethyl or monoethyl ether (methyl glycol or ethyl glycol), ethylene glycol dimethyl ether (diglyme); ketones such as acetone or butanone; amides such as acetamide, N-methylpyrrolidone (NMP), dimethylacetamide or dimethylformamide (DMF); nitriles such as acetonitrile; sulfoxides such as dimethyl sulfoxide (DMSO); carbon disulfide; carboxylic acids such as formic acid or acetic acid; nitro compounds such as nitromethane or nitrobenzene; esters such as ethyl acetate or mixtures of the solvents mentioned.

The reaction of the compounds of formula II with compounds of formula III is analoguesly to the coupling of peptides. The condensation reaction of formula II with formula III is preferably carried out in an inert solvent as indicated above in the presence of a dehydrating agent, such as, dicyclohexylcarbodiimide (DCC), N-(3-dimethylaminopropyl)-N'-ethyl-carbodiimide-hydrochlorid (EDC) or diisopropylcarbodiimide (DIC), further for instance in the presence of an anhydride of propanphosphonic acid (see Angew. Chem. 1980, 92, 129), diphenylphosphorylazide or 2-ethoxy-N-ethoxycarbonyl-1,2-dihydroquinoline.

Particularly preferred is the presence of a coupling agent, such as TBTU (O-(benzotriazol-1-yl)-N,N,N',N'-bis-(tetramethylene)-uronium tetrafluoroborate) or O-(benzotriazol-1-yl)-N,N,N',N'-bis-(tetramethylene)-uronium hexafluorophosphate.

A compound of formula II in which X is a reactive esterified OH group can be synthesized by reacting a compound of formula II in which X is OH with HOBt (1-hydroxybenzotriazole) or N-hydroxysuccinimide (e.g. in the standard works such as Houben-Weyl, Methoden der organischen Chemie [Methods of Organic Chemistry], Georg-Thieme-Verlag, Stuttgart).

For the preparation of compounds of the formula I in which $R^2$ or $R^3$ are —C(=NH)—NH—, a compound of formula I in which $R^2$ and $R^3$ are H can be treated with an amidinating agent. The preferred amidinating agent is 1-amidino-3,5-dimethylpyrazole (DPFN), which is employed, in particular, in the form of its nitrate, or pyrazole-1-carboxamidine. The reaction is expediently carried out with addition of a base such as triethylamine or ethyldiisopropylamine in an inert solvent or solvent mixture, e.g. DMF at temperatures between 0° and 150° C., preferably between 60° and 120° C.

For the preparation of compounds of the formula I in which $R^4$ is unsubstituted or substituted biphenyl, 5-(3,4-dimethoxyphenyl)-thiophen-2-yl or 5-[2,2']bithiophenyl, an appropriate compound of the formula I in which $R^4$ is phenyl chloride, phenyl bromide, phenyl iodide, thiophenyl chloride, thiophenyl bromide or thiophenyl iodide can be reacted with the appropriate boronic acid derivatives in a Suzuki type coupling reaction. This reaction is expediently carried out under Palladium catalysis with different phosphines as coordination ligands, e.g. $Pd(P(Ph)_3)_2$, $Pd(II)Cl_2dppf$, $PdOAc_2+P(R^*)_3$ ($R^*$=phenyl, cyclohexyl, tert-butyl) etc. in the presence of a base such as potassium carbonate, caesium carbonate, DBU, NaOH, in an inert solvent or solvent mixture, e.g. DMF or 1,4-dioxane at temperatures between 0° and 150°, preferably between 60° and 120°. Depending on the conditions used, the reaction time is between a few minutes and a number of days. The boronic acid derivatives can be prepared by conventional methods or are commercially available. The reactions can be carried out in analogy to the methods indicated in Suzuki et al., J. Am. Chem. Soc. 1989, 111, 314ff., Suzuki et al., Chem. Rev. 1995, 95, 2457ff and G. C. Fu et al. Angew. Chem 1998, 110, 3586.

A base of the formula I can be converted into the associated acid addition salt using an acid, for example by reaction of equivalent amounts of the base and of the acid in an inert solvent such as ethanol and subsequent evaporation. Acids which give physiologically acceptable salts are particularly suitable for this reaction. Thus inorganic acids can be used, e.g. sulfuric acid, nitric acid, hydrohalic acids such as hydrochloric acid or hydrobromic acid, phosphoric acids such as orthophosphoric acid, sulfamic acid, furthermore organic acids, in particular aliphatic, alicyclic, araliphatic, aromatic or heterocyclic mono- or polybasic carboxylic, sulfonic or sulfumic acids, e.g. formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, p-toluenesulfonic acid, naphthalenemono- and disulfonic acids or laurylsulfuric acid. Salts with physiologically unacceptable acids, e.g. picrates, can be used for the isolation and/or purification of the compounds of the formula I.

On the other hand, compounds of the formula I with bases (e.g. sodium or potassium hydroxide or carbonate) can be converted into the corresponding metal salts, in particular alkali metal or alkaline earth metal salts, or into the corresponding ammonium salts.

The invention furthermore relates to pharmaceutical preparations comprising at least one compound of the formula I and/or one of its physiologically acceptable salts, which are prepared, in particular, in an non-chemical way. In this case, the compounds of the formula I can be brought into a suitable dose form together with at least one solid, liquid and/or semi-liquid excipient or auxiliary and, if appropriate, in combination with one or more other active compounds.

These preparations can be used as medicaments in human or veterinary medicine. Possible excipients are organic or inorganic substances which are suitable for enteral (e.g. oral) or parenteral administration or topical application and do not react with the novel compounds, for example water, vegetable oils, benzyl alcohols, alkylene glycols, polyethylene glycols, glyceryl triacetate, gelatin, carbohydrates such as lactose or starch, magnesium stearate, talc and petroleum jelly. Tablets, pills, coated tablets, capsules, powders, granules, syrups, juices or drops are used, in particular, for oral administration, suppositories are used for rectal administration, solutions, preferably oily or aqueous solutions, furthermore suspensions, emulsions or implants, are used for parenteral administration and ointments, creams or powders are used for topical application. The novel compounds can also be lyophilized and the lyophilizates obtained used, for example, for the production of injection preparations. The preparations indicated can be sterilized and/or can contain auxiliaries such as lubricants, preservatives, stabilizers and/or wetting agents, emulsifiers, salts for affecting the osmotic pressure, buffer substances, colourants, flavourings and/or one or more other active compounds, e.g. one or more vitamins.

The compounds of the formula I and their physiologically acceptable salts act as adhesion receptor antagonists, in particular glycoprotein IbIX antagonists, and can be employed for the prophylaxis and/or therapy of thrombotic disorders and sequelae deriving therefrom. The disorders are acute coronary syndromes, angina pectoris, myocardial infarct, peripheral circulatory disorders, stroke, transient ischaemic attacks, arteriosclerosis and reocclusion/restenosis after angioplasty/stent implantation.

In this case, the substances according to the invention are as a rule administered in the dose of the glycoprotein IIbIIIa antagonist ReoPro® of preferably between approximately 1 and 500 mg, in particular between 5 and 100 mg, per dose unit. The daily dose is preferably between approximately 0.02 and 10 mg/kg of body weight. The specific dose for each patient depends, however, on all sorts of factors, for example on the efficacy of the specific compound employed, on the age, body weight, general state of health and sex, on the diet, on the time and route of administration, and on the excretion rate, pharmaceutical combination and severity of the particular disorder to which the therapy applies. Oral administration is preferred.

Above and below, all temperatures are indicated in ° C. In the following examples, "customary working-up" for solution reactions means: if necessary, water is added, if necessary, depending on the constitution of the final product, the mixture is adjusted to pHs between 2 and 10 and extracted with ethyl acetate or dichloromethane, the organic phase is separated off, dried over sodium sulfate and evaporated, and the residue is purified by chromatography on silica gel and/or by crystallization.

"Customary working-up" for solid-phase reactions means: the crude reaction is filtered and washed with DMF twice, then sucessively with methanol and methylene chloride three times, and finally once with methyl tert-butyl ether. The resin is then dried in vacuo.

Mass spectrometry (MS) apparatuses Kratos Maldi III and Finnigan LCQ. (M+H)$^+$ values or M$^+$ values are determined.

EXAMPLES

Example 1

3 grams (1.62 mmol) of p-nitrophenylcarbonate resin (1) [Novabiochem: 0.54 mmol/g loading) is suspended in 30 ml of DMF then 8.1 mmol of C (3-Aminomethyl-cyclohexyl)-methylamine is added at room temperature. The reaction is then heated to 55° and left to stir for two days. The crude reaction is then customary worked up for solid-phase reactions affording the resin bound bis amine (2).

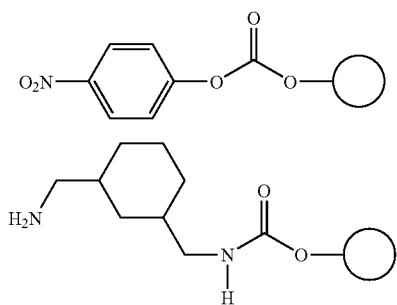

Analogously, by reaction of the p-nitrophenylcarbonate resin (1) with the bis amines of formula III

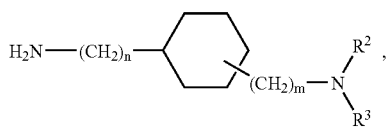

in which R$^2$ and R$^3$ are H, excluding C-(3-aminomethyl-cyclohexyl)-methylamine, and n and m have the meanings indicated in claim 1 the following resin bound bis amines are obtained:
cyclohexane-1,3-diamine, resin bound:
3-aminomethyl-cyclohexylamine, resin bound;
3-aminoethyl-cyclohexylamine, resin bound;
3-aminopropyl-cyclohexylamine, resin bound;
C-(3-aminopropyl-cyclohexyl)-methylamine, resin bound;
C-(3-aminoethyl-cyclohexyl)-ethylamine, resin bound;
C-(3-aminopropyl-cyclohexyl)-propylamine, resin bound;
cyclohexane-1,4-diamine, resin bound;
4-aminomethyl-cyclohexylamine, resin bound;
4-aminoethyl-cyclohexylamine, resin bound;
4-aminopropyl-cyclohexylamine, resin bound;
C-(4-aminomethyl-cyclohexyl)-methylamine, resin bound;
C-(4-aminoethyl-cyclohexyl)-methylamine, resin bound;
C-(4-aminopropyl-cyclohexyl)-methylamine, resin bound;
C-4-aminoethyl-cyclohexyl)-ethylamine, resin bound and
C-(4-aminopropyl-cyclohexyl)-propylamine, resin bound.

Example 2

1. Synthesis of Fmoc Protected Anthranilic Acid 29.15 mmol of anthranilic acid is taken in 100 ml of 1,4 dioxane then 145 mmol of sodium bicarbonate in 20 ml of water is added. Next, 32 mmol of Fmoc-Cl is added and the reaction is left to stir overnight at room temperature. The reaction is then concentrated in vacuo and customary worked up for solution reactions. The resulting solid is triturated in ethyl ether affording the pure product.

2. Coupling of Fmoc Protected Anthranilic Acid to Resin 1 gram of resin (2) is suspended in 10 ml of DMF. The reaction is then treated with 1.62 mmol of Fmoc protected anthranilic acid, 1.62 mmol of HBTU, and 1.62 mmol of triethyl amine. The reaction is then allowed to shake overnight at room temperature. After customary working up, the resin is dried in vacuo affording resin bound anthranilic acid (3).

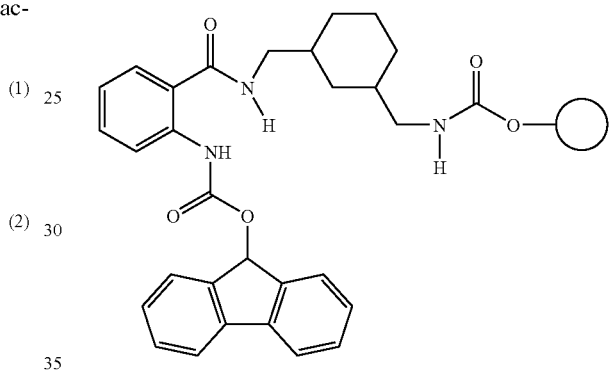

3. Cleavage of Fmoc Protected Group 1 gram resin (3) is suspended in 10 ml of 20% piperidine/DMF and shaken for 1.5 hours at room temperature. The reaction is then customary worked up for solid-phase reactions affording the free aniline (4).

4. Aldehyde Condensation and Ring Closure 100 mg resin (4) is suspended in 1 ml of dimethyl acetamide then 200 µl of acetic acid is added followed by the addition of 2.16 mmol of benzaldehyde. The reaction is then heated to 800 for two days. The reaction is then cooled to room temperature and customary worked up for solid-phase reactions affording the resin (5).

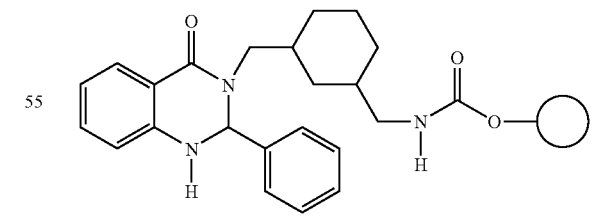

5. Oxidation to Quinazolinone 100 mg resin (5) is suspended in 4 ml solution of 36 mg of DDQ in DMF. Then the reaction is allowed to shake overnight at room temperature. The reaction is then customary worked up for solid-phase reactions affording quinazolinone (6) resin bound.

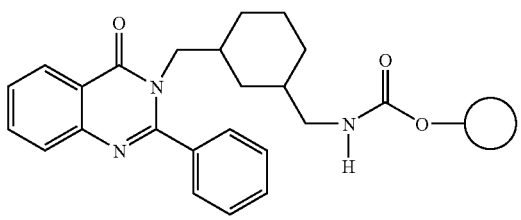

(6)

6. Cleavage of the Final Product 3-(3-aminomethyl-cyclohexylmethyl)-2-phenyl-3H-quinazolin-4-one 100 mg of resin (6) is suspended in 2 ml of a 50% trifluoroacetic acid/methylene chloride solution and shaken for 1.5 hours at room temperature. Customary working up for solid-phase reactions afforded 3-(3-aminomethyl-cyclohexylmethyl)-2-phenyl-3H-quinazolin-4-one;

MS calc.: 347.4 found: 348.2.

Example 3

Analogously to example 2, by reaction of resin (2) with a compound of formula IIa

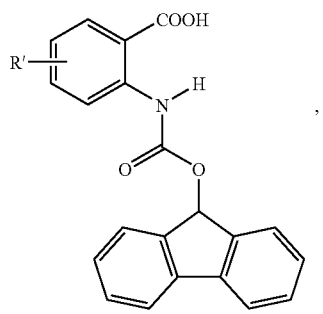

IIa cleavage of the Fmoc protecting group and reaction with benzaldehyde, oxidation and cleavage from the solid phase, the following compounds are obtained
with R'=3-Cl in formula IIa
3-(3-aminomethyl-cyclohexylmethyl)-6-chloro-2-phenyl-3H-quinazolin-4-one;
MS calc.: 381.9 found: 382.2;
with R'=3-CH$_2$ in formula IIa
3-(3-aminomethyl-cyclohexylmethyl)-6-methyl-2-phenyl-3H-quinazolin-4-one;
MS calc.: 361.5 found: 362.2;
with R'=4-Cl in formula IIa
3-(3-aminomethyl-cyclohexylmethyl)-7-chloro-2-phenyl-3H-quinazolin-4-one;
MS calc.: 381.9 found: 382.2;
with R'=3-OCH, in formula IIa
3-(3-aminomethyl-cyclohexylmethyl)-6-methoxy-2-phenyl-3H-quinazolin-4-one;
MS calc.: 377.5.

Analogously to example 2, by reaction of resin (2) with a compound of formula IIa, cleavage of the Fmoc protecting group and reaction with 2-methyl-benzaldehyde, oxidation and cleavage from the solid phase, the following compounds are obtained
with R'=3-Cl in formula IIa
3-(3-aminomethyl-cyclohexylmethyl)-6-chloro-2-(2-methylphenyl)-3H-quinazolin-4-one;
MS calc.: 395.9 found: 396.2;
with R'=3-CH$_3$ in formula IIa
3-(3-aminomethyl-cyclohexylmethyl)-6-methyl-2-(2-methylphenyl)-3H-quinazolin-4-one;
MS calc.: 375.5 found: 376.2;
with R' =4-Cl in formula IIa
3-(3-aminomethyl-cyclohexylmethyl)-7-chloro-2-(2-methylphenyl)-3H-quinazolin-4-one;
MS calc.: 395.9 found: 396.2;
with R'=3-OCH, in formula IIa
3-(3-aminomethyl-cyclohexylmethyl)-6-methoxy-2-(2-methylphenyl)-3H-quinazolin-4-one;
MS calc.: 391.5 found: 392.2;
with R'=H in formula IIa
3-(3-aminomethyl-cyclohexylmethyl)-2-(2-methylphenyl)-3H-quinazolin-4-one;
MS calc.: 361.5 found: 362.2.

Analogously to example 2, by reaction of resin (2) with a compound of formula IIa, cleavage of the Fmoc protecting group and reaction with 3-methyl-benzaldehyde, oxidation and cleavage from the solid phase, the following compounds are obtained
with R'=3-Cl in formula IIa
3-(3-aminomethyl-cyclohexylmethyl)-6-chloro-2-(3-methylphenyl)-3H-quinazolin-4-one;
MS calc.: 395.9 found: 396.2;
with R'=3-CH$_3$ in formula IIa
3-(3-aminomethyl-cyclohexylmethyl)-6-methyl-2-(3-methylphenyl)-3H-quinazolin-4-one;
MS calc.: 375.5 found: 376.2;
with R'=4-Cl in formula IIa
3-(3-aminomethyl-cyclohexylmethyl)-7-chloro-2-(3-methylphenyl)-3H-quinazolin-4-one;
MS calc.: 395.9 found: 396.2;
with R'=H in formula IIa
3-(3-aminomethyl-cyclohexylmethyl)-6-methoxy-2-(3-methylphenyl)-3H-quinazolin-4-one;
MS calc.: 391.5 found: 392.2;
with R'=H in formula IIa
3-(3-aminomethyl-cyclohexylmethyl-2-(3-methylphenyl)-3H-quinazolin-4-one;
MS calc.: 361.5 found: 362.2.

Analogously to example 2, by reaction of resin (2) with a compound of formula IIa, cleavage of the Fmoc protecting group and reaction with 4-methyl-benzaldehyde, oxidation and cleavage from the solid phase, the following compounds are obtained
with R'=3-Cl in formula IIa
3-(3-aminomethyl-cyclohexylmethyl)-6-chloro-2-(4-methylphenyl)-3H-quinazolin-4-one;
MS calc.: 395.9 found: 396.2;
with R'=3-CH, in formula IIa
3-(3-aminomethyl-cyclohexylmethyl)-6-methyl-2-(4-methylphenyl)-3H-quinazolin-4-one;
MS calc.: 375.5 found: 376.2;
with R'=4-Cl in formula IIa
3-(3-aminomethyl-cyclohexylmethyl)-7-chloro-2-(4-methylphenyl)-3H-quinazolin 4-one;
MS calc.: 395.9 found: 396.2;
with R' =3-OCH$_3$ in formula IIa
3-(3-aminomethyl-cyclohexylmethyl)-6-methoxy-2-(4-methylphenyl)-3H-quinazolin-4-one;
MS calc.: 391.5 found: 392.2;
with R' =H in formula IIa
3-(3-aminomethyl-cyclohexylmethyl)-2-(4-methylphenyl)-3H-quinazolin-4-one;
MS calc.: 361.5 found: 362.2.

Analogously to example 2, by reaction of resin (2) with a compound of formula IIa, cleavage of the Fmoc protecting group and reaction with 4-tert-butyl-benzaldehyde, oxidation and cleavage from the solid phase, the following compounds are obtained with R'=3-Cl in formula IIa
3-(3-aminomethyl-cyclohexylmethyl)-6-chloro-2-(4-tert-butylphenyl)-3H-quinazolin-4-one;
MS calc.: 438.0 found: 438.2;

with R' =3-CH$_3$ in formula IIa
3-(3-aminomethyl-cyclohexylmethyl)-6-methyl-2-(4-tert-butylphenyl)-3H-quinazolin-4-one;
MS calc.: 417.6 found: 418.2;

with R' =4-Cl in formula IIa
3-(3-aminomethyl-cyclohexylmethyl)-7-chloro-2-(4-tert-butylphenyl)-3H-quinazolin-4-one;
MS calc.: 438.0 found: 438.2;

with R'=3-OCH$_3$ in formula IIa
3-(3-aminomethyl-cyclohexylmethyl)-6-methoxy-2-(4-tert-butylphenyl)-3H-quinazolin-4-one;
MS calc.: 433.6 found: 434.2;

with R' =H in formula IIa
3-(3-aminomethyl-cyclohexylmethyl-2-(4-tert-butylphenyl)-3H-quinazolin-4-one;
MS calc.: 403.6 found: 404.3.

Analogously to example 2, by reaction of resin (2) with a compound of formula IIa, cleavage of the Fmoc protecting group and reaction with 3-chloro-benzaldehyde, oxidation and cleavage from the solid phase, the following compounds are obtained with R'=3-Cl in formula IIa
3-(3-aminomethyl-cyclohexylmethyl)-6-chloro-2-(3-chlorophenyl)-3H-quinazolin-4-one;
MS calc.: 416.4 found: 416.2;

with R' =3-CH$_3$ in formula IIa
3-(3-aminomethyl-cyclohexylmethyl)-6-methyl-2-(3-chlorophenyl)-3H-quinazolin-4-one;
MS calc.: 395.9 found: 396.2;

with R' =4-Cl in formula IIa
3-(3-aminomethyl-cyclohexylmethyl)-7-chloro-2-(3-chlorophenyl)-3H-quinazolin-4-one;
MS calc.: 416.3 found: 416.2;

with R' =3-OCH$_3$ in formula IIa
3-(3-aminomethyl-cyclohexylmethyl)-6-methoxy-2-(3-chlorophenyl)-3H-quinazolin-4-one;
MS calc.: 411.9 found: 412.1;

with R' =H in formula IIa
3-(3-aminomethyl-cyclohexylmethyl)-2-(3-chlorophenyl)-3H-quinazolin-4-one;
MS calc.: 381.9 found: 382.2.

Analogously to example 2, by reaction of resin (2) with a compound of formula IIa, cleavage of the Fmoc protecting group and reaction with 4-methoxy-benzaldehyde, oxidation and cleavage from the solid phase, the following compounds are obtained with R' =3-Cl in formula IIa
3-(3-aminomethyl-cyclohexylmethyl)-6-chloro-2-(4-methoxyphenyl)-3H-quinazolin-4-one;
MS calc. 411.9 found: 412.2;

with R' =3-CH, in formula IIa
3-(3-aminomethyl-cyclohexylmethyl)-6-methyl-2-(4-methoxyphenyl)-3H-quinazolin-4-one;
MS calc.: 391.5 found: 392.2;

with R'=4-Cl in formula IIa
3-(3-aminomethyl-cyclohexylmethyl)-7-chloro-2-(4-methoxyphenyl)-3H-quinazolin-4-one;
MS calc.: 411.9 found: 412.2;

with R'=3-OCH$_3$ in formula IIa
3-(3-aminomethyl-cyclohexylmethyl)-6-methoxy-2-(4-methoxyphenyl)-3H-quinazolin-4-one;
MS calc.: 407.5 found: 408.2;

with R' =H in formula IIa
3-(3-aminomethyl-cyclohexylmethyl-2-(4-methoxyphenyl)-3H-quinazolin-4-one;
MS calc.: 377.5 found: 378.2.

Analogously to example 2, by reaction of resin (2) with a compound of formula IIa, cleavage of the Fmoc protecting group and reaction with 3-methoxy-benzaldehyde, oxidation and cleavage from the solid phase, the following compounds are obtained with R' =3-Cl in formula IIa
3-(3-aminomethyl-cyclohexylmethyl)-6-chloro-2-(3-methoxyphenyl)-3H-quinazolin-4-one;
MS calc.: 411.9 found: 412.1;

with R'=3-CH$_3$ in formula IIa
3-(3-aminomethyl-cyclohexylmethyl)-6-methyl-2-(3-methoxyphenyl)-3H-quinazolin-4-one;
MS calc.: 391.5 found: 392.2;

with R' =4-Cl in formula IIa
3-(3-aminomethyl-cyclohexylmethyl)-7-chloro-2-(3-methoxyphenyl)-3H-quinazolin-4-one;
MS calc.: 411.9 found: 412.2;

with R'=3-OCH$_3$ in formula IIa
3-(3-aminomethyl-cyclohexylmethyl)-6-methoxy-2-(3-methoxyphenyl)-3H-quinazolin-4-one;
MS calc.: 407.5 found: 408.2;

with R'=H in formula IIa
3-(3-aminomethyl-cyclohexylmethyl-2-(3-methoxyphenyl)-3H-quinazolin-4-one;
MS calc.: 377.5 found: 378.2.

Example 4

Analogously to example 2, by reaction of resin (2) with a compound of formula IIa

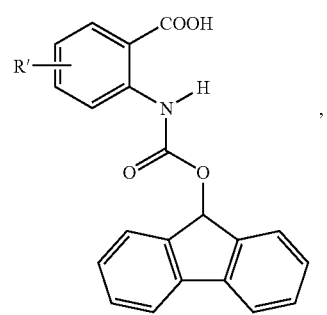

IIa cleavage of the Fmoc protecting group and reaction with 3,4,5-trimethoxybenzaldehyde, oxidation and cleavage from the solid phase, the following compounds are obtained with R'=3-Cl in formula IIa
3-(3-aminomethyl-cyclohexylmethyl)-6-chloro-2-(3,4,5-trimethoxyphenyl)-3H-quinazolin-4-one;

with R'=3-CH$_3$ in formula IIa
3-(3-aminomethyl-cyclohexylmethyl)-6-methyl-2-(3,4,5-trimethoxyphenyl)-3H-quinazolin-4-one;

with R'=4-Cl in formula IIa 3-(3-aminomethyl-cyclohexylmethyl)-7-chloro-2-(3,4,5-trimethoxyphenyl)-3H-quinazolin-4-one;

with R'=3-OCH$_3$ in formula IIa
3-(3-aminomethyl-cyclohexylmethyl)$_6$-methoxy-2-(3,4,5-trimethoxyphenyl)-3H-quinazolin-4-one;

with R'=H in formula IIa 3-(3-aminomethyl-cyclohexylmethyl)-2-(3,4,5-trimethoxyphenyl)-3H-quinazolin-4-one.

Analogously to example 2, by reaction of resin (2) with a compound of formula IIa, cleavage of the Fmoc protecting group and reaction with 3,4-dimethoxybenzaldehyde, oxidation and cleavage from the solid phase, the following compounds are obtained
with R' =3-Cl in formula IIa
3-(3-aminomethyl-cyclohexylmethyl)-6-chloro-2-(3,4-dimethoxyphenyl)-3H-quinazolin-4-one;
with $R^1$=3-CH$_3$ in formula IIa
3-(3-aminomethyl-cyclohexylmethyl)-6-methyl-2-(3,4-dimethoxyphenyl)$_3$H-quinazolin-4-one;
with R' =4-Cl in formula IIa
3-(3-aminomethyl-cyclohexylmethyl)-7-chloro-2-(3,4-dimethoxyphenyl)-3H-quinazolin-4-one;
with R'=3-OCH, in formula IIa
3-(3-aminomethyl-cyclohexylmethyl)-6-methoxy-2-(3,4-dimethoxyphenyl)-3H-quinazolin-4-one;
with R' =H in formula IIa
3-(3-aminomethyl-cyclohexylmethyl)-2-(3,4-dimethoxyphenyl)-3H-quinazolin-4-one.

Example 5

Analogously to example 2, by reaction of resin (2) with a compound of formula IIa, cleavage of the Fmoc protecting group and reaction with [2,2']bithiophenyl-5-carbaldehyde, oxidation and cleavage from the solid phase, the following compounds are obtained
with R' =3-Cl in formula IIa
3-(3-aminomethyl-cyclohexylmethyl)-2-[2,2'-bithiophenyl-5-yl-6-chloro-3H-quinazolin-one;
MS calc.: 470.1 found: 470.1;
with R'=3-CH, in formula IIa
3-(3-aminomethyl-cyclohexylmethyl)-2-[2,2']bithiophenyl-5-yl-6-methyl-3H-quinazolin-4-one;
MS calc.: 449.6 found: 450.1;
with R' =4-Cl in formula IIa
3-(3-aminomethyl-cyclohexyl-methyl)-2-[2,2]bithiophenyl-5-yl-7-chloro-3H-quinazolin-4-one;
MS calc.: 470.1 found: 470.1;
with R' =3-OCH$_3$ in formula IIa
3-(3-aminomethyl-cyclohexylmethyl)-2-[(2,2']bithiophenyl-5-yl-6-methoxy-3H-quinazolin-4-one;
MS calc.: 465.6 found: 466.1;
with R'=H in formula IIa
3-(3-aminomethyl-cyclohexylmethyl)-2-[2,2']bithiophenyl-5-yl-3H-quinazolin-4-one;
MS calc.: 435.6 found: 436.1.

Example 6

Analogously to example 2, by reaction of resin (2) with a compound of formula IIa, cleavage of the Fmoc protecting group and reaction with 3-furan-2-yl-propenal, oxidation and cleavage from the solid phase, the following compounds are obtained
with R' =3-Cl in formula IIa
3-(3-aminomethyl-cyclohexylmethyl)-6-chloro-2-(2-furan-2-yl-vinyl)-3H-quinazolin-4-one;
MS calc.: 397.9 found: 398.2;
with R'=3-CH$_3$ in formula IIa
3-(3-aminomethyl-cyclohexylmethyl)-6-methyl-2-(2-furan-2-yl-vinyl)-3H-quinazolin-4-one;
MS calc.: 377.5 found: 378.3;
with R'=4-Cl in formula IIa
3-(3-aminomethyl-cyclohexylmethyl)-7-chloro-2-(2-furan-2-yl-vinyl)-3H-quinazolin one;
MS calc.: 397.9 found: 398.2;
with R'=3-OCH$_3$ in formula IIa
3-(3-aminomethyl-cyclohexylmethyl)-6-methoxy-2-(2-furan-2-yl-vinyl)-3H-quinazolin-4-one;
MS calc.: 393.5 found: 394.3;
with R'=H in formula IIa
3-(3-aminomethyl-cyclohexylmethyl)-2-(2-furan-2-yl-vinyl)-3H-quinazolin-4-one;
MS calc.: 363.5 found: 364.2.

Example 7

Analogously to example 2, by reaction of resin (2) with a compound of formula IIa, cleavage of the Fmoc protecting group and reaction with cyclohexanecarbaldehyde, oxidation and cleavage from the solid phase, the following compounds are obtained
with R' =3-Cl in formula IIa
3-(3-aminomethyl-cyclohexylmethyl)-6-chloro-2-cyclohexyl-3H-quinazolin-4-one;
MS calc.: 388.0 found: 388.2;
with R'=3-CH, in formula IIa
3-(3-aminomethyl-cyclohexylmethyl)-6-methyl-2-cyclohexyl-3H-quinazolin-4-one;
MS calc.: 367.5 found: 368.3;
with R'=4-Cl in formula IIa
3-(3-aminomethyl-cyclohexylmethyl)-7-chloro-2-cyclohexyl-3H-quinazolin-4-one;
MS calc.: 388.0 found; 388.2;
with R'=3-OCH$_3$ in formula IIa
3-(3-aminomethyl-cyclohexylmethyl)-6-methoxy-2-cyclohexyl-3H-quinazolin-4-one;
MS calc.: 383.5 found: 384.3;
with R'=H in formula IIa
3-(3-aminomethyl-cyclohexylmethyl)-2-cyclohexyl-3H-quinazolin-4-one;
MS calc.: 353.5 found: 354.3.

Example 8

Analogously to example 2, by reaction of resin (2) with a compound of formula IIa, cleavage of the Fmoc protecting group and reaction with 3-phenyl-propionaldehyde, oxidation and cleavage from the solid phase, the following compounds are obtained
with R'=3-Cl in formula IIa 3-(3-aminomethyl-cyclohexylmethyl)-6-chloro-2-phenylethyl-3H-quinazolin-4-one;
MS calc.: 410.0 found: 410.3;
with R'=3-CH$_3$ in formula IIa 3-(3-aminomethyl-cyclohexylmethyl)-6-methyl-2-phenylethyl-3H-quinazolin-4-one;
MS calc.: 389.5 found: 390.4;
with R'=4-CH$_3$ in formula IIa
3-(3-aminomethyl-cyclohexylmethyl)-7-chloro-2-phenylethyl-3H-quinazolin-4-one;
MS calc.: 410.0 found: 410.3;
with R'=3-OCH$_3$ in formula IIa
3-(3-aminomethyl-cyclohexylmethyl)-6-methoxy-2-phenylethyl-3H-quinazolin-4-one;
MS calc.: 405.5 found: 406.3;
with R'=H in formula IIa
3-(3-aminomethyl-cyclohexylmethyl)-2-phenylethyl-3H-quinazolin-4-one;
MS calc.: 375.5 found: 376.4.

Example 9

Analogously to example 2, by reaction of resin (2) with a compound of formula IIa, cleavage of the Fmoc protecting group and reaction with biphenyl-4-carbaldehyde, oxidation and cleavage from the solid phase, the following compounds are obtained with R' =3-Cl in formula IIa
3-(3-aminomethyl-cyclohexylmethyl)-2-biphenyl-4-yl-6-chloro-3H-quinazolin-4-one;
  MS calc.: 458.0 found: 458.2;
with R'=3-CH$_3$ in formula IIa
3-(3-aminomethyl-cyclohexylmethyl)-2-biphenyl-4-yl-6-methyl-3H-quinazolin-4-one;
  MS calc.: 437.6 found: 438.2;
with R'=4-Cl in formula IIa 3-(3-aminomethyl-cyclohexylmethyl)-2-biphenyl-4-yl-7-chloro-3H-quinazolin-4-one;
  MS calc.: 458.0 found: 458.2;
with R' =3-OCH$_3$ in formula IIa
3-(3-aminomethyl-cyclohexylmethyl)-2-biphenyl-4-yl-6-methoxy-3H-quinazolin-4-one;
  MS calc.: 453.6 found: 454.2;
with R' =H in formula IIa
3-(3-aminomethyl-cyclohexylmethyl)-2-biphenyl-4-yl-3H-quinazolin-4-one;
  MS calc.: 423.6 found: 424.2.

Example 10

Analogously to example 2, by reaction of resin (2) with a compound of formula IIa, cleavage of the Fmoc protecting group and reaction with thiophene-3-carbaldehyde, oxidation and cleavage from the solid phase, the following compounds are obtained with R'=3-Cl in formula IIa
3-(3-aminomethyl-cyclohexylmethyl)-2-thiophenyl-3-yl-6-chloro-3H-quinazolin-4-one;
  MS calc.: 387.9 found: 388.2;
with R'=3-CH$_3$ in formula IIa
3-(3-aminomethyl-cyclohexylmethyl)-2-thiophenyl-3-yl-6-methyl-3H-quinazolin-4-one;
  MS calc.: 367.5 found: 368.2;
with R'=4-Cl in formula IIa
3-(3-aminomethyl-cyclohexylmethyl)-2-thiophenyl-3-yl-7-chloro-3H-quinazolin-4-one;
  MS calc.: 387.9 found: 388.2;
with R' =3-OCH$_3$ in formula IIa
3-(3-aminomethyl-cyclohexylmethyl)-2-thiophenyl-3-yl-6-methoxy-3H-quinazolin-4-one;
  MS calc.: 383.5; found: 384.2;
with R' =H in formula IIa
3-(3-aminomethyl-cyclohexylmethyl)-2-thiophenyl-3-yl-3H-quinazolin-4-one;
  MS calc.: 353.5 found: 354.2.

Analogously to example 2, by reaction of resin (2) with a compound of formula IIa, cleavage of the Fmoc protecting group and reaction with thiophene-2-carbaldehyde, oxidation and cleavage from the solid phase, the following compounds are obtained with R' =3-Cl in formula IIa
3-(3-aminomethyl-cyclohexylmethyl)-2-thiophenyl-2-yl-chloro-3H-quinazolin-4-one;
  MS calc.: 387.9 found: 388.2;
with R'=3-CH$_3$ in formula IIa
3-(3-aminomethyl-cyclohexylmethyl)-2-thiophenyl-2-yl-6-methyl-3H-quinazolin-4-one;
  MS calc.: 367.5 found: 368.2;
with R'=H in formula IIa
3-(3-aminomethyl-cyclohexylmethyl)-2-thiophenyl-2-yl-7-chloro-3H-quinazolin-4-one;
  MS calc.: 387.9 found: 388.1;
with R'=3-OCH$_3$ in formula IIa
3-(3-aminomethyl-cyclohexylmethyl)-2-thiophenyl-2-yl-3-methoxy-3H-quinazolin-4-one;
  MS calc.: 383.5 found: 384.2;
with R' =H in formula IIa
3-(3-aminomethyl-cyclohexylmethyl)-2-thiophenyl-2-yl-3H-quinazolin-4-one;
  MS calc.: 353.5 found: 354.2.

Example 11

Analogously to example 2, by reaction of resin (2) with a compound of formula IIa, cleavage of the Fmoc protecting group and reaction with naphthalene-2-carbaldehyde, oxidation and cleavage from the solid phase, the following compounds are obtained with R'=3-Cl in formula IIa
3-(3-aminomethyl-cyclohexylmethyl)-2-naphthalen-2-yl-6-chloro-3H-quinazolin-4-one;
  MS calc.: 432.0 found: 432.2;
with R'=3-CH, in formula IIa
3-(3-aminomethyl-cyclohexylmethyl)-2-naphthalen-2-yl-6-methyl-3H-quinazolin-4-one;
  MS calc.: 411.6 found: 412.2;
with R'=4-CH$_3$ in formula IIa
3-(3-aminomethyl-cyclohexylmethyl)-2-naphthalen-2-yl-7-chloro-3H-quinazolin-4-one;
  MS calc.: 432.0 found: 432.2;
with R'=3-C H$_3$ in formula IIa
3-(3-aminomethyl-cyclohexylmethyl)-2-naphthalen-2-yl-6-methoxy-3H-quinazolin-4-one;
  MS calc.: 427.6 found: 428.2;
with R'=H in formula IIa
3-(3-aminomethyl-cyclohexylmethyl)-2-naphthalen-2-yl-3H-quinazolin-4-one;
  MS calc.: 397.5 found: 398.2.

Analogously to example 2, by reaction of resin (2) with a compound of formula IIa, cleavage of the Fmoc protecting group and reaction with naphthalene-1-carbaldehyde, oxidation and cleavage from the solid phase, the following compounds are obtained with R'=3-Cl in formula IIa
3-(3-aminomethyl-cyclohexylmethyl)-2-naphthalen-1-yl-chloro-3H-quinazolin-4-one;
  MS calc.: 432.0 found: 432.2;
with R'=3-CH$_3$ in formula IIa
3-(3-aminomethyl-cyclohexylmethyl)-2-naphthalen-1-yl-methyl-3H-quinazolin-4-one;
  MS calc.: 411.6 found: 412.2;
with R'=4-Cl in formula IIa
3-(3-aminomethyl-cyclohexylmethyl)-2-naphthalen-1-yl-7-chloro-3H-quinazolin-4-one;
  MS calc.: 432.0 found: 432.2;
with R'=3-OCH, in formula IIa
3-(3-aminomethyl-cyclohexylmethyl)-2-naphthalen-1-yl-6-methoxy-3H-quinazolin-4-one;
  MS calc.: 427.6 found: 428.2;
with R'=H in formula IIa
3-(3-aminomethyl-cyclohexylmethyl)-2-naphthalen-1-yl-3H-quinazolin-4-one;
  MS calc.: 397.5 found: 398.2.

Example 12

Analogously to example 2, by reaction of resin (2) with a compound of formula IIa, cleavage of the Fmoc protecting group and reaction with 3-phenyl-propenal, oxidation and cleavage from the solid phase, the following compounds are obtained with R'=3-Cl in formula IIa
3-(3-aminomethyl-cyclohexylmethyl)-2-styryl-6-chloro-3H-quinazolin-4-one;
MS calc.: 407.9 found: 408.2;
with R'=3-CH$_3$ in formula IIa
3-(3-aminomethyl-cyclohexylmethyl)-2-styryl-6-methyl-3H-quinazolin-4-one;
MS calc.: 387.5 found: 388.3;
with R'=4-Cl in formula IIa
3-(3-aminomethyl-cyclohexylmethyl)-2-styryl-7-chloro-3H-quinazolin-4-one;
MS calc.: 407.9 found: 408.2;
with R'=3-OCH, in formula IIa
3-(3-aminomethyl-cyclohexylmethyl)-2-styryl-6-methoxy-3H-quinazolin-4-one;
MS calc.: 403.5 found: 404.3;
with R'=H in formula IIa
3-(3-aminomethyl-cyclohexylmethyl)-2-styryl-3H-quinazolin-4-one;
MS calc.: 373.5 found: 374.3.

Example 13

Analogously to example 2, by reaction of resin (2) with a compound of formula IIa, cleavage of the Fmoc protecting group and reaction with benzofuran-5-carbaldehyde, oxidation and cleavage from the solid phase, the following compounds are obtained with R'=3-Cl in formula IIa
3-(3-aminomethyl-cyclohexyl-methyl)-2-benzofuran-5-yl-6-chloro-3H-quinazolin-4-one;
MS calc.: 421.9 found: 422.2;
with R'=3-CH$_3$ in formula IIa
3-(3-aminomethyl-cyclohexylmethyl)-2-benzofuran-5-yl-methyl-3H-quinazolin-4-one;
MS calc.: 401.5 found: 402.2;
with R'=4-Cl in formula IIa
3-(3-aminomethyl-cyclohexylmethyl)-2-benzofuran-5-yl-7-chloro-3H-quinazolin-4-one;
MS calc.: 421.9 found: 422.2;
with R'=3-OCH$_3$ in formula IIa
3-(3-aminomethyl-cyclohexylmethyl)-2-benzofuran-5-yl-6-methoxy-3H-quinazolin-4-one;
MS calc.: 417.5 found: 418.1;
with R'=H in formula IIa
3-(3-aminomethyl-cyclohexylmethyl)-2-benzofuran-5-yl-3H-quinazolin-4-one;
MS calc,: 387.5 found: 388.2.

Example 14

Analogously to example 2, by reaction of resin (2) with a compound of formula IIa, cleavage of the Fmoc protecting group and reaction with 3-(4-dimethylamino-phenyl)-propenal, oxidation and cleavage from the solid phase, the following compounds are obtained with R'=3-Cl in formula IIa
3-(3-aminomethyl-cyclohexylmethyl)-2-[2-(4-dimethylamino-phenyl)-vinyl]-6-chloro-3H-quinazolin-4-one;
MS calc.: 451.0;
with R'=3-CH, in formula IIa
3-(3-aminomethyl-cyclohexylmethyl)-2-[2-(4-dimethylamino-phenyl)-vinyl]6-methoxy-3H-quinazolin-4-one;
MS calc.: 430.6;
with R'=4-Cl in formula IIa 3-(3-aminomethyl-cyclohexylmethyl)-2-[2-(4-dimethylamino-phenyl)-vinyl]-7-chloro-3H-quinazolin-4-one;
MS calc.: 451.0;
with R'=3-OCH$_3$ in formula IIa
3-(3-aminomethyl-cyclohexylmethyl)-2-[2-(4-dimethylamino-phenyl)-vinyl]-6-methoxy-3H-quinazolin-4-one;
MS calc.: 446.6;
with R'=H in formula IIa
3-(3-aminomethyl-cyclohexylmethyl)-2-[2-(4-dimethylamino-phenyl)-vinyl]-3H-quinazolin-4-one;
MS calc.: 416.6;

Analogously to example 2, by reaction of resin (2) with a compound of formula IIa, cleavage of the Fmoc protecting group and reaction with 3-(2,5-dimethoxy-phenyl)-propenal, oxidation and cleavage from the solid phase, the following compounds are obtained with R'=3-Cl in formula IIa
3-(3-aminomethyl-cyclohexylmethyl)-2-[2-(2,5-dimethoxy-phenyl)-vinyl]-6-chloro-3H-quinazolin-4-one;
with R' =3-CH, in formula IIa
3-(3-aminomethyl-cyclohexylmethyl)-2-[2-(2,5-dimethoxy-phenyl)-vinyl]-methyl-3H-quinazolin-4-one;
with R'=4-Cl in formula IIa
3-(3-aminomethyl-cyclohexylmethyl)-2-[2-(2,5-dimethyoxy-phenyl)-vinyl]-7-chloro-3H-quinazolin-4-one;
with R'=3-OCH$_3$ in formula IIa
3-(3-aminomethyl-cyclohexylmethyl)-2-[2-(2,5-dimethoxy-phenyl)-vinyl]6-methoxy-3H-quinazolin-4-one;
with R'=H in formula IIa 3-(3-aminomethyl-cyclohexylmethyl)-2-[2-(2,5-dimethoxy-phenyl)-vinyl]-3H-quinazolin-4-one.

Example 15

Analogously to example 2, by reaction of resin (2) with a compound of formula IIa, cleavage of the Fmoc protecting group and reaction with 4-bromo-benzaldehyde, Suzuki-reaction with 2,4-dimethoxyphenyl boronic acid as indicated afterwards, oxidation and cleavage from the solid phase, the following compounds are obtained with R'=3-Cl in formula IIa
3-(3-aminomethyl-cyclohexylmethyl)-2-(2',4'-dimethoxy-biphenyl-4-yl)-6-chloro-3H-quinazolin-4-one;
with R'=3-CH, in formula IIa
3-(3-aminomethyl-cyclohexylmethyl)-2-(2',4'-dimethoxy-biphenyl-4-yl)-6-methyl-3H-quinazolin-4-one;
with R'=4-Cl in formula IIa
3-(3-aminomethyl-cyclohexylmethyl)-2-(2',4'-dimethoxy-biphenyl-4-yl)-7-chloro-3H-quinazolin-one;
with R'=3-OCH$_3$ in formula IIa
3-(3-aminomethyl-cyclohexylmethyl)-2-(2',4'-dimethoxy-biphenyl-4-yl)-6-methoxy-3H-quinazolin-4-one;
with R'=H in formula IIa
3-(3-aminomethyl-cyclohexylmethyl)-2-(2',4'-dimethoxy-biphenyl-4-yl)-3H-quinazolin-4-one.

Suzuki reaction according to G. C. Fu et al., Angew. Chem. 1998, 110, 3586–3587:

1 gram of resin bound 3-(3-aminomethyl-cyclohexylmethyl)-2-(4-bromophenyl)-3H-quinazolin-4-one is suspended in 10 ml of 1,4-dioxane. The reaction is then treated with 1.62 mmol Cs$_2$CO$_3$, 1.62 mmol of 2,4- dimethoxyphenyl boronic acid and 10 mol % ([Pd$_2$(dba)$_3$]+ P(tert-Bu)$_3$). The reaction is then allowed to shake at 80° until conversion is complete. After cooling the reaction mixture, it is worked up as is customary.

Analogously to example 2, by reaction of resin (2) with a compound of formula IIa, cleavage of the Fmoc protecting group and reaction with 4-bromo-benzaldehyde, Suzuki-reaction with 3,5-dimethoxyphenyl boronic acid as indicated afterwards, oxidation and cleavage from the solid phase, the following compounds are obtained
with R'=3-Cl in formula IIa
3-(3-aminomethyl-cyclohexylmethyl)-2-(3',5'-dimethoxy-biphenyl-4-yl)-6-chloro-3H-quinazolin-4-one;
with R'=3-CH: in formula IIa
3-(3-aminomethyl-cyclohexylmethyl)-2-(3',5'-dimethoxy-biphenyl-4-yl)-6-methyl-3H-quinazolin-4-one;
with R'=4-Cl in formula IIa
3-(3-aminomethyl-cyclohexylmethyl)-2-(3',5'-dimethoxy-biphenyl-4-yl)-7-chloro-3H-quinazolin-4-one;
with R'=3-OCH$_3$ in formula IIa
3-(3-aminomethyl-cyclohexylmethyl)-2-(3',5'-dimethoxy-biphenyl-4-yl)-6-methoxy-3H-quinazolin-4-one;
with R'=H in formula IIa
3-(3-aminomethyl-cyclohexyl-methyl)-2-(3',5'-dimethoxy-biphenyl-4-yl)-3H-quinazolin-4-one.

Analogously to example 2, by reaction of resin (2) with a compound of formula IIa, cleavage of the Fmoc protecting group and reaction with 5-bromo-thiophenyl-2-carbaldehyde, Suzuki-reaction with 3,4-dimethoxyphenyl boronic acid as indicated afterwards, oxidation and cleavage from the solid phase, the following compounds are obtained
with R' =3-Cl in formula IIa
3-(3-aminomethyl-cyclohexylmethyl)-2-[5-(2,4-dimethoxy-phenyl)-2-thiophenyl]6-chloro-3H-quinazolin-4-one;
with R'=3-CH, in formula IIa
3-(3-aminomethyl-cyclohexylmethyl)-2-[5-(2,4-dimethoxy-phenyl)-2-thiophenyl]-6-methyl-3H-quinazolin-4-one;
with R'=4-Cl in formula IIa
3-(3-aminomethyl-cyclohexylmethyl)-2-[5-(2,4-dimethoxy-phenyl)-2-thiophenyl]-7-chloro-3H-quinazolin-one;
with R'=3-OCH$_3$ in formula IIa
3-(3-aminomethyl-cyclohexylmethyl)-2-[5-(2,4-dimethoxy-phenyl)-thiophen-2-yl]-6-methoxy-3H-quinazolin-4-one;
with R'=H in formula IIa
3-(3-aminomethyl-cyclohexylmethyl)-2-[5-(2,4-dimethoxy-phenyl)-thiophen-2-yl]-3H-quinazolin-4-one.

The following examples relate to pharmaceutical preparations:

Example A

Injection Vials

A solution of 100 g of an active compound of the formula I and 5 g of disodium hydrogenphosphate is adjusted to pH 6.5 in 3 l of double-distilled water using 2N hydrochloric acid, sterile-filtered, dispensed into injection vials, lyophilized under sterile conditions and aseptically sealed. Each injection vial contains 5 mg of active compound.

Example B

Suppositories

A mixture of 20 g of an active compound of the formula I is melted with 100 g of soya lecithin and 1400 g of cocoa butter, poured into moulds and allowed to cool. Each suppository contains 20 mg of active compound.

Example C

Solution

A solution is prepared from 1 g of an active compound of the formula I, 9.38 g of NaH$_2$PO$_4$2H$_2$O, 28.48 g of Na$_2$HPO$_4$, 12H$_2$O and 0.1 g of benzalkonium chloride in 940 ml of double-distilled water. The mixture is adjusted to pH 6.8, made up to 1 l and sterilized by irradiation. This solution can be used in the form of eye drops.

Example D

Ointment 500 mg of an active compound of the formula I is mixed with 99.5 g of petroleum jelly under aseptic conditions.

Example E

Tablets

A mixture of 1 kg of active compound of the formula I, 4 kg of lactose, 1.2 kg of potato starch, 0.2 g of talc and 0.1 kg of magnesium stearate is compressed in a customary manner to give tablets such that each tablet contains 10 mg of active compound.

Example F

Coated Tablets

Analogously to Example E, tablets are pressed which are then coated with a coating of sucrose, potato starch, talc, tragacanth and colourant in a customary manner.

Example G

Capsules 2 kg of active compound of the formula I are dispensed into hard gelatin capsules in a customary manner such that each capsule contains 20 mg of the active compound.

Example H

Ampules

A solution of 1 kg of active compound of the formula I in 60 ml of double-distilled water is sterile-filtered, dispensed into ampoules, lyophilized under sterile conditions and aseptically sealed. Each ampoule contains 10 mg of active compound.

What is claimed is:

1. A compound selected from the group consisting of:
   a) 3-(3-aminomethyl-cyclohexylmethyl)-2-[2,2']bithiophenyl-5-yl-6-methoxy-3H-quinazolin-4-one,
   b) 3-(3-aminomethyl-cyclohexylmethyl)-2-naphthalen-1-yl-6-methoxy-3H-quinazolin-4-one;
   c) 3-(3-aminomethyl-cyclohexylmethyl)-2-naphthalen-1-yi-6-methyl-3H-quinazolin-4-one;
   d) 3-(3-aminomethyl-cyclohexylmethyl)-2-naphthalen-1-yi-3H-quinazolin-4-one;
   e) 3-(3-aminomethyl-cyclohexylmethyl)-2-naphthalen-2-yi-6-methoxy-3H-quinazolin-4-one;
   f) 3-(3-aminomethyl-cyclohexylmethyl)-2-naphthalen-2-yl-3-H-quinazolin-4-one;
   g) 3-(3-aminomethyl-cyclohexylmethyl)-2-naphthalen-2-yl-6-methyl-3H-quinazolin-4-one;
   h) 3-(3-aminomethyl-cyclohexylmethyl)-6-chloro-2-naphthalen-2-yl-3H-quinazolin-4-one; and
   i) 3-(3-aminomethyl-cyclohexylmethyl)-7-chloro-2-naphthalen-2-yl-3H-quinazolin-4-one;

and physiologically acceptable salts and solvates thereof.

2. A process for preparing a compound of claim 1, comprising the step of: treating a solvate or hydrate of a compound of claim 1 with a solvolysing or hydrogenolysing agent.

3. A pharmaceutical composition, comprising:
 a compound according to claim 1 or a pharmaceutically acceptable salt or solvate thereof; and a pharmaceutically acceptable excipient.

4. A method of antagonizing glycoprotein IbIX receptors, comprising the step of:
 administering an effective amount of a compound according to claim 1 or a pharmaceutically acceptable salt or solvate thereof to a patient in need thereof.

5. A method of controlling a thrombotic disorder and sequelae deriving therefrom, comprising the step of:
 administering an effective amount of a compound according to claim 1 or a pharmaceutically acceptable salt or solvate thereof to a patient in need thereof.

6. A method of preventing adhesion on a foreign surface, in contact with a patient, comprising the step of:
 administering an effective amount of a compound according to claim 1 or a pharmaceutically acceptable salt or solvate thereof to said patient.

7. A method according to claim 5, wherein said sequelae is myocardial infarct, arteriosclerosis, angina pectoris, acute coronary syndromes, peripheral circulatory disorders, stroke, transient ischaemic attacks, or reocclusion/restenosis after angioplasty/stent implantations.

8. A method according to claim 6, wherein said foreign surface is the surface of an implant, catheter, or heart pacemaker.

* * * * *